(12) United States Patent
Hogan

(10) Patent No.: US 6,264,637 B1
(45) Date of Patent: *Jul. 24, 2001

(54) MARKING SYRINGE

(76) Inventor: Thomas Hogan, 2420 Westport Cir., Marietta, GA (US) 30064

( * ) Notice: Subject to any disclaimer, the term of this patent is extended or adjusted under 35 U.S.C. 154(b) by 0 days.

This patent is subject to a terminal disclaimer.

(21) Appl. No.: 09/389,774

(22) Filed: Sep. 3, 1999

Related U.S. Application Data

(63) Continuation-in-part of application No. 08/883,268, filed on Jun. 26, 1997, now Pat. No. 5,961,494.

(51) Int. Cl.$^7$ ..................................................... A61M 5/00
(52) U.S. Cl. .......................... 604/191; 604/223; 606/116; 81/9.22
(58) Field of Search ..................................... 604/191, 181, 604/187, 116, 61, 207, 208–211, 223, 224, 115, 218, 130; 222/135, 129, 137, 391, 327, 82; 606/116, 117; 128/DIG. 6; 81/9.22

(56) References Cited

U.S. PATENT DOCUMENTS

| | | |
|---|---|---|
| 3,949,746 | 4/1976 | Wallach . |
| 4,152,412 | 5/1979 | Brewer . |
| 4,214,490 | 7/1980 | Chizek . |
| 4,726,594 | 2/1988 | Benke . |
| 5,135,507 | 8/1992 | Haber et al. ........................ 604/187 |
| 5,147,307 | 9/1992 | Gluck ................................... 604/116 |
| 5,192,270 | 3/1993 | Carswell, Jr. ....................... 604/116 |
| 5,326,001 | 7/1994 | Holmquist et al. . |
| 5,376,079 | * 12/1994 | Holm .................................. 604/191 |
| 5,591,135 | 1/1997 | Sullivan .............................. 604/211 |
| 5,935,111 | * 8/1999 | Bunyan ............................... 604/191 |
| 5,961,494 | * 10/1999 | Hogan ................................. 604/191 |

FOREIGN PATENT DOCUMENTS 2 120 554   12/1983   (GB) .

* cited by examiner

Primary Examiner—Ronald K. Stright, Jr.
(74) Attorney, Agent, or Firm—Troutman, Sanders LLP; Wm. Brook Lafferty

(57) ABSTRACT

A marking syringe which allows an individual using the syringe to inject a fluid such as a vaccine into an animal and, at the same time, mark the location of the injection on the animal. More specifically, the marking syringe includes a vaccine syringe and an ink dispenser connected to a handle. Activation of the handle simultaneously activates the vaccine syringe and the ink dispenser. The vaccine syringe is connected to a source of vaccine and a source of ink is provided. After connection of the vaccine and ink sources, the syringe needle is inserted into the animal and a syringe handle is actuated. As the handle is actuated, a vaccine syringe and an ink dispenser both discharge their contents. The position of the ink dispenser relative to the vaccine syringe is such that the discharged ink marks the animal in the approximate location of the vaccine injection.

16 Claims, 4 Drawing Sheets

MARKING SYRINGE

CROSS-REFERENCE TO RELATED APPLICATION

This application is a Continuation-in-Part of U.S. application Ser. No. 08/883,268, filed Jun. 26, 1997, now U.S. Pat. No. 5,961,494.

FIELD OF THE INVENTION

This invention relates in general to devices for injecting medicines into animals and, more particularly, to devices which mark the animal concurrently upon injecting the animal.

BACKGROUND OF THE INVENTION

The days of farmers independently operating small family farms profitably are, for the most part, a distant memory. Today's successful farmers rely heavily on quantity, quality and efficiency to operate their businesses successfully. In the hog industry, for example, a successful business operation may include hundreds, if not thousands, of hogs. In such an operation, overhead is kept low by employing only a handful of people to perform all aspects of the maintenance of the hogs, including breeding, feeding, treating, and selling.

The recognized need to increase efficiency in the hog production industry has given rise to the development of numerous devices for assisting hog farming operations. Computers are heavily used to track information related to genetics, feed consumption, and environmental factors, often providing feedback information concerning the quality of the final product. Such feedback allows a farmer to modify production processes for better outcomes. The efforts of farmers to increase profitability and productivity have also been assisted by both the pharmaceutical and nutrition industries. Each of these industries has produced a vast array of nutrition supplements and medicinal regimens to keep hogs healthier and, ultimately, more valuable. The negative aspect of these new regimens is that they require increased man-hours to administer. For instance, it is not uncommon for each hog in a herd to require 7–9 medicinal injections per year—which is nearly double the number required only a decade ago. In today's hog farming environment, both the number of injections per hog and the number of hogs in a typical operation are increasing at the same time the number of employees on hand to maintain the hogs is decreasing. Thus, the maximization of personnel resources and delivery methods becomes ever more critical.

Aside from sheer volume, the delivery of injectable medicines to animals is complicated by the temperaments and behavior of the animals themselves. As a rule, hogs are generally not pleased at the prospect of receiving injections. Furthermore, there is no practical way to restrict movement of the hogs during the injection process. As a result, a hog who is about to receive or has received his medicine may be difficult to control and may intermingle with hogs who have not yet been injected. Accordingly, the possibility exists that certain hogs may go without their intended injections while others mistakenly receive multiple doses. Either scenario—leaving an animal unvaccinated or overvaccinating an animal carry significant downfalls. Such mistakes in the administration of medicines could, in one extreme, threaten the well-being of the animals. In another extreme, the result may be toxic levels of medicines in the end products.

Various methods and devices have been developed to combat these inefficiencies, although recent changes to industry standards and production methods for hogs have rendered many of these solutions obsolete. For instance, as recently as twenty years ago it was a standard practice for farmers to deliver injectable medicines without paying particular attention to the specific location of the injections, either on the hogs or relative to one another. Subsequent research has indicated that this practice resulted in problems such as the delivery of medicines to areas to which they were not optimally assimilated into the bloodstream of the hog. Just as bad, delivery of the medicines to a disadvantageous location could blemish or damage the surrounding tissue, thereby devaluating the final meat product.

A good example of an early medicine delivery device which manifested the above referenced problems can be found in U.S. Pat. No. 3,949,746 (the '746 patent) issued to Wallach. The medicine delivery device of the '746 patent comprises a hypodermic syringe apparatus and includes a contact member having an apertured front plate and a hydraulic cylinder reciprocated mounting plate supporting a group of hypodermic needles in slidable registry with the front plate openings. The needles pierce a liquid absorbing web backing the front plate. Each needle is connected by a flexible tube to an adjustable stroke piston pump and then to liquid injectable holding receptacles. The pistons are simultaneously actuated by a motor driven cam carrying shaft. The motor is controlled by a handle carried switch to rotate the shaft one turn. The shaft carrying cam also controls the flow of the liquid to the handle cylinder, and the absorbent pad is connected to a source of antiseptic. A marking pad is carried by the handle front wall to identify the puncture area.

Because of the complicated nature and resulting expense of the device of the '746 patent, it never found widespread use in the livestock industry, where profit margins are typically too low to support either the purchase or the continued maintenance required by such a complicated device. Additionally, the manner in which the injections are delivered by the '746 patent is now considered unacceptable for several reasons. First, livestock experts now agree that delivering a large number of treatments in essentially the same location may limit the effectiveness of some medicines and may even be detrimental to the animal. Secondly, the former practice of delivering injectable treatments to "high yield" meat areas such as the rump (as shown in the '746 patent) reduces the quality of the salable meat from that area and reduces the profitability of the animal.

More recently, individual syringes have been developed which allow the farmer to apply an injection in any desired location using a single-handled manual syringe. One such syringe is the ST5 "Easy Vac" Automatic Syringe, manufactured by Forlong & Massey d/b/a Simcro Tech of New Zealand and distributed in the United States by Vac-Pac Incorporated of Marietta, Ga. (1-800-793-1671). Typically, the Easy-Vac syringe is used in conjunction with a so-called "paint stick". In livestock operations, the paint stick is a well known device which resembles a large grease pencil and is used to mark the hog which has received the injection. If used properly, the farmer injects the animal with a syringe held in one hand and marks the injected on the animal with a paint stick held in the other hand. Proper use of the paint stick identifies the animal as one which has been injected and, if used properly, may also provide a visible indication of the general location of the injection, although there is no assurance that a mark made by a paint stick has been placed in proximity to the location of the injection. Not only are these benefits helpful in the delivery of future injections, but they serve as the basis for a "quality review" of injection locations by a supervisor whose duty it is to insure that injections are being administered to the proper locations.

Even this improved method of delivering injections poses serious problems for the farmer. First, it is extremely easy for a low-paid manual laborer who is delivering the injections to take a shortcut by injecting the animal in an easily accessible but improper area (such as the rump), then use the paint stick to mark the animal where the injection should have been given, such as in the neck. Secondly, even if used properly, both of the hands of the farmer are occupied, making it extremely difficult to control the animal in any meaningful way. Often, an animal will escape control of the farmer after being injected and before being marked, resulting in the potential risk of an animal receiving multiple injections.

Accordingly, a need exists for an apparatus for injecting hogs and other livestock which delivers injections easily, accurately and reliably. There is an additional need for such an apparatus which will mark both the animal injected and the location of the injection on the animal concurrent with the delivery of the injection. Finally, there exists a need for such an apparatus which can be operated with one hand, leaving the farmer one hand free to control the animal, protect himself or deliver a second injection and mark with a second apparatus substantially simultaneously.

SUMMARY OF THE INVENTION

The present invention is a marking syringe which allows an individual using the marking syringe to inject a fluid such as a vaccine into an animal and, at the same time, mark the location of the injection on the animal and the animal being injected. More specifically, the marking syringe of the present invention includes a vaccine syringe connected to a source of vaccine and an ink dispenser. A handle is operatively connected to both the vaccine syringe and the ink dispenser. After connection to the vaccine and ink sources, the syringe needle is inserted into the animal and the handle is actuated. As the handle is actuated, the vaccine syringe and the ink dispenser discharge their contents substantially simultaneously. The position of the ink dispenser relative to the vaccine syringe is such that the discharged ink marks the animal in the approximate location of the vaccine injection through the needle.

The marking syringe of the present invention carries many advantages over current injecting and marking systems. First, because the handle activates both the vaccine syringe and the ink dispenser substantially simultaneously, the marking syringe of the present invention can be easily operated with one hand, leaving the user's other hand free to control the animal or to operate a second marking syringe. The operation of a second marking syringe poses obvious advantages, in that one user could apply twice as many injections in roughly the same amount of time, thereby cutting in half the number of man-hours needed to accomplish the task.

Another advantage of the marking syringe of the present invention is that it applies a mark to the animal in close proximity to the actual injection by the needle. Unlike current popular methods of marking, the user cannot apply the injection with the needle in one area of the animal and apply the mark to a different area.

Yet another advantage the marking syringe of the present invention is its simplicity of use. Specifically, the marking syringe of the present invention does not require power of any type and, thus, can be easily used in remote locations. Additionally, the marking syringe of the present invention is easily disassembled for cleaning or replacement of failed parts.

Accordingly, it is an object of the present invention to provide an apparatus for injecting hogs and other livestock which delivers injections easily, accurately and reliably. It is another object of the present invention to provide an apparatus which will mark both the animal injected and the location of the injection on the animal concurrent with the delivery of the vaccine injection. It is yet another object of the present invention to provide an apparatus which can accomplish the foregoing and be operated with one hand, leaving the user one hand free to control the animal, protect himself or deliver a second injection and mark with a second apparatus substantially simultaneously.

DETAILED DESCRIPTION

Before describing the details of the present invention, it will be appreciated that the term "ink" is used herein to describe marking substances of a wide variety of types including liquid ink, dry ink, liquid or gas particles suspended in gas, grease pencils, and many others. The use of the term "ink" herein and in the claims hereof is not intended in any way to be limiting.

Figure 1:
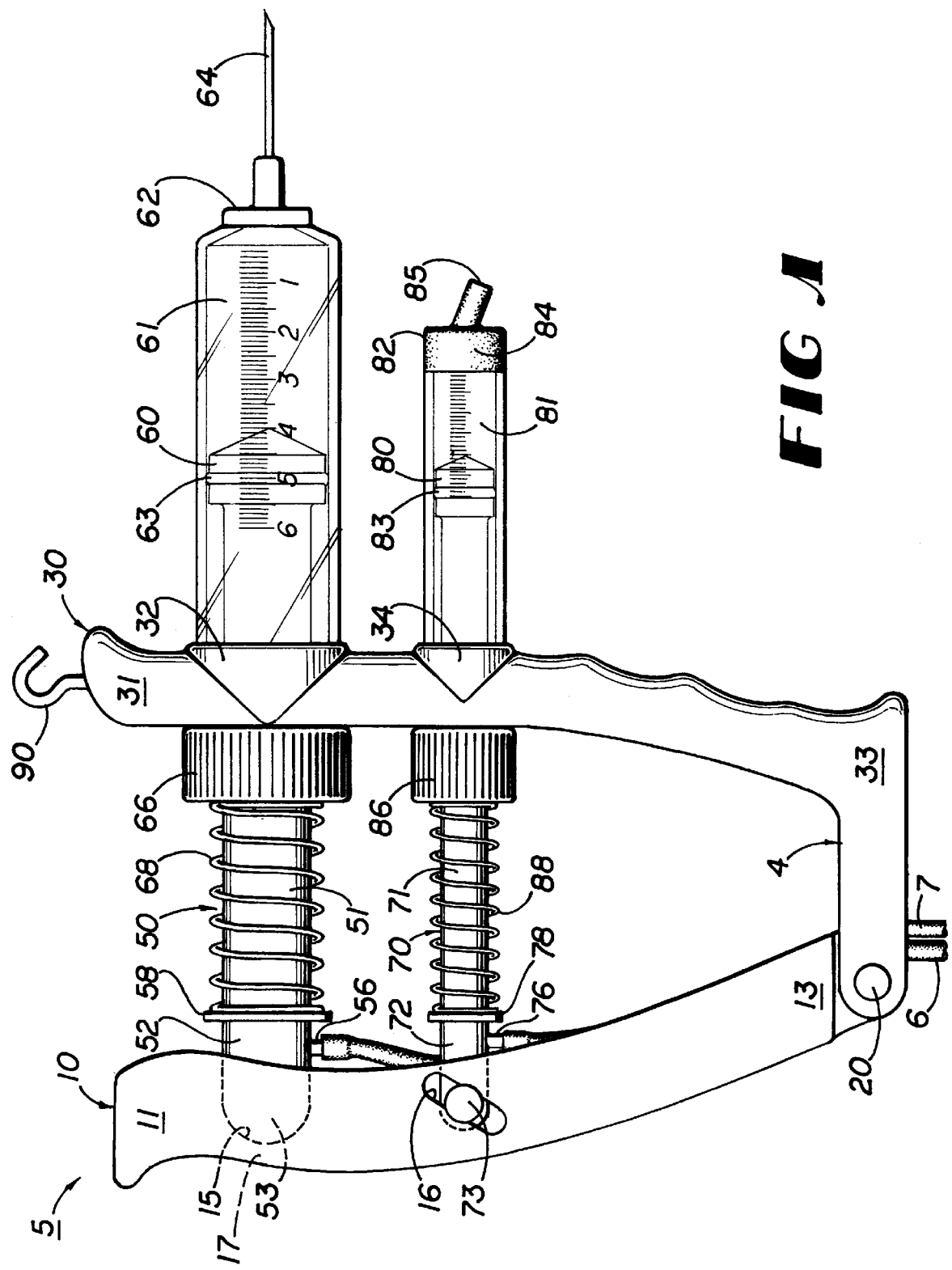
FIG. 1 is an illustration of an exemplary embodiment of the present invention in a typical operating environment.

Referring now to the drawings, FIG. 1 is an illustration of a first preferred embodiment of the present invention, which shows a marking syringe for simultaneously injecting a vaccine or other substance into an animal while placing an identifying mark on the animal in the vicinity of the injection.

As can be seen in FIG. 1, the marking syringe 5 of the first preferred embodiment of the present invention comprises, generally, a syringe handle 4 operatively connected to a vaccine syringe 50 and an ink dispenser 70. The syringe handle 4 comprises a first syringe handle 10 pivotally connected to a second syringe handle 30. The first syringe handle 10 is elongated, having a first end 11 and a second end 13. The handle 10 is generally shaped for comfortable receipt into the palm portion of the hand of the user. A socket 15 is located intermediate the first end 11 and the second end 13. An ink dispenser interface 17 is located generally adjacent to the socket 15 on the handle 10. The handle 10 has a pivot hole at its second end 13.

The second syringe handle 30 of marking syringe 5 is also elongated and has a first end 31 and a second end 33. The first end 31 of the second syringe handle 30 may securely receive a hook 90 for storage of the marking syringe 5 between uses. The second syringe handle 30 is configured to function as a finger grip for the user. The second end 33 of the second syringe handle 30 is sized to slidably straddle the second end 13 of the first handle 10 and has a pivot hole through its thickness. The second handle 30 includes an integral vaccine syringe collar 32 and an integral ink dispenser collar 34.

During assembly, the second end 33 of the second syringe handle 30 is positioned over the second end 13 of the first syringe handle 10 such that the pivot holes in the ends 13 and 33 are axially aligned. Thereafter, a pivot pin 20 is inserted through the aligned holes and appropriately secured therein in any number of ways, including deforming distal ends of the pivot pin 20 so that the diameter of the pivot pin 20 is larger at the points of deformation than the diameter of the pivot pin receiving holes, thereby preventing withdrawal of the pivot pin 20 through the pivot pin receiving holes. After the pivot pin 20 is properly positioned and secured, the second syringe handle 30 rotates about the axis of the pivot pin 20 in a plane defined by the second syringe handle 30 and the first syringe handle 10. In use, the first and second handles 10, 30 are initially in a spread position. The user can then grip the first and second handles 10, 30 and squeeze them into a closed position as the handles 10, 30 pivot about the pin 20.

The vaccine syringe 50 is mounted between the handles 10, 30 by means of the collar 32 on the second syringe handle 30 and the socket 15 on the first syringe handle 10. The vaccine syringe 50 comprises a vaccine syringe head 52 with a ball 53, an extendible vaccine syringe shaft 51, a vaccine syringe biasing spring 68, a vaccine syringe plunger 60, a vaccine dosage chamber 61, a vaccine syringe needle fastener 62, and a needle 64. In order to connect the syringe 50 to the handle 4, the dosage chamber 61 is threaded into the handle collar 32 of handle 30, and the vaccine syringe head 52 is connected to the handle 10 by engaging the ball 53 of the head 52 into the socket 15 of the handle 10 in a well known manner.

The head 52 is hollow and further comprises a vaccine syringe nipple 56, and a vaccine syringe stop flange 58. The vaccine syringe nipple 56 may be integral to the hollow vaccine syringe head 52 and is sized to securely receive a syringe vaccine hose 6. Vaccine is delivered to the hollow interior cavity of the head 52 via the vaccine hose 6 which is connected to a vaccine source (not shown). The vaccine syringe stop flange 58 extends laterally about the periphery of the vaccine syringe head 52.

The extendible vaccine syringe shaft 51 interconnects the syringe head 52 and the plunger 60. The shaft 51 has an interior axial conduit (not shown) which communicates at one end with the interior cavity of the head 52 and at the other end with an interior axial conduit (not shown) through the plunger 60. The syringe shaft 51 extends through a vaccine syringe collar 32 of the second syringe handle 30 and into the vaccine dosage chamber 61. In order to vary the amount of dosage, the shaft 51 has a vaccine dosage adjust valve 66. The dosage adjust valve 66 comprises a collar that engages the plunger 60 on one end and is threaded onto the shaft 51.

The vaccine syringe plunger 60 slides within the vaccine dosage chamber 61. An O-ring 63 creates a liquid tight seal between the periphery of the plunger 60 and the interior wall of the dosage chamber 61. The plunger 60 has a check valve (not shown) within its interior axial conduit that allows liquid to pass only in the direction toward the needle end of the syringe 50.

The vaccine dosage chamber 61 is formed of a translucent or transparent material and is secured at its first end to the vaccine syringe collar 32. The vaccine dosage chamber 61 may be scored with incremental graduations to assist a user in dosage measurements. At its second end, the vaccine dosage chamber 61 removably receives a vaccine syringe needle fastener 62. The vaccine syringe needle fastener 62 is fitted to capture a needle 64. A check valve (not shown) is fitted within the needle fastener 62 to allow liquid flow only out of the needle 64.

A vaccine syringe biasing spring 68 is disposed around the vaccine syringe shaft 51 between the vaccine syringe stop flange 58 and the vaccine dosage adjust valve 66. The biasing spring 68 is a compression spring which serves to return the handles 10, 30 to their initial spread position after being squeezed closed by the user.

When the handles 10, 30 are squeezed together, the plunger 60 moves within the dosage chamber 61. The movement of the plunger 60 closes the check valve within the plunger 60 to force vaccine in the dosage chamber 61 through the check valve within the needle fastener 62 and out through the needle 64. When the handles 10, 30 are released by the user, the check valve within the needle fastener 62 closes to preclude fluid or air being drawn into the dosage chamber 61 through the needle 64. Simultaneously, the check valve within the plunger 60 opens so that vaccine is drawn into the dosage chamber 61 through the nipple 56, the hollow head 52, the conduit within the shaft 51, and the conduit within the plunger 60. By turning the dosage adjust valve 66, the length of the shaft 51 is changed. Changing the length of the shaft 51 changes the length of the plunger stroke, and the amount of medicine delivered through the needle 64 is accordingly changed.

Similarly, in a first preferred embodiment, the ink dispenser 70 is mounted between the handles 10, 30 by means of the collar 34 on the handle 30 and the first handle ink dispenser interface 17 on the handle 10. In the first preferred embodiment, the ink is in liquid form, the ink dispenser 70 is a syringe, and the ink dispenser interface 17 is a slot 16. The ink syringe 70 comprises an ink syringe head 72 with a pin 73 extending therefrom, an extendible ink syringe shaft 71, an ink syringe biasing spring 88, an ink syringe plunger 80, an ink dosage chamber 81, and an ink discharge orifice 82. In order to connect the syringe 70 to the handle 4, the dosage chamber 81 is threaded into the handle collar 34 of the second syringe handle 30, and the ink syringe head 72 is connected to the first syringe handle 10 by engaging the pin 73 of the head 72 into the slot 16 of the first syringe handle 10 in a well known manner. The combination of the slot 16 and the pin 73 assures axial alignment of the plunger 80 with the ink dosage chamber 81.

In an alternate embodiment, the pumping action accomplished by the handles 10,30 being squeezed together may be replaced by actuation of a source of compressed gas in communication with both the ink syringe plunger 80 and the plunger 60. When the source of compressed gas is actuated by a manual device such as a trigger, the source of compressed gas discharges an amount of gas sufficient to advance both the ink syringe plunger 80 and the plunger 60 within the ink dosage chamber 81 and the dosage chamber 61 so as to discharge chamber contents in the above-described manner. The trigger may be any of a wide variety of configurations suitable for such functionality, and may be positioned on the marking syringe 5 proximal to the position of a finger, thumb, or the needle end of the marking syringe 5. Alternate embodiments are also specifically contemplated wherein the trigger is remote from the marking syringe 5 and actuated by a foot, voice, visual or other type of command.

The head 72 is hollow and further comprises an ink syringe nipple 76 and a ink syringe stop flange 78. The ink syringe nipple 76 may be integral to the hollow ink syringe head 72 and is sized to securely receive a syringe ink hose 7. Ink is delivered to the hollow interior cavity of the head 72 via the ink hose 7 which is connected to an ink source (not shown). The ink syringe stop flange 78 extends laterally about the periphery of the ink syringe head 72.

The extendible ink syringe shaft 71 interconnects the syringe head 72 and the plunger 80. The shaft 71 has an interior axial conduit (not shown) which communicates at one end with the interior cavity of the head 72 and at the other end with an interior axial conduit (not shown) through the plunger 80. The syringe shaft 71 extends through the ink syringe collar 34 of the second syringe handle 30 and into the ink dosage chamber 81. In order to vary the amount of ink dispensed, the shaft 71 has a ink dosage adjust valve 86. The dosage adjust valve 86 comprises a collar that engages the plunger 80 on one end and is threaded onto the shaft 71.

The ink syringe plunger 80 slides within the ink dosage chamber 61. An O-ring 83 creates a liquid tight seal between the periphery of the plunger 80 and the interior wall of the dosage chamber 81. The plunger 80 has a check valve (not shown) within its interior axial conduit that allows liquid to pass only in the direction toward the needle end of the syringe 70.

The ink dosage chamber 81 is formed of a translucent or transparent material and is secured at its first end to the ink syringe collar 34. The ink dosage chamber 81 may be scored with incremental graduations to assist a user in dosage measurements. At its second end, the ink dosage chamber 81 has the discharge orifice 82. A check valve (not shown) is fitted within the discharge orifice 82 to allow ink flow only out of the discharge orifice 82. The discharge orifice 82 has a body portion 84 and an end portion 85 which is set at an angle to the axis of the cylindrical dosage chamber 81. By rotating the discharge orifice 82 on the cylindrical dosage chamber 81, the end portion 85 may be aimed and thereby control the location of the resulting mark with respect to the needle 64.

An ink syringe biasing spring 88 is disposed around the ink syringe shaft 71 between the ink syringe stop flange 78 and the ink dosage adjust valve 86. The biasing spring 88 is a compression spring which serves to return the handles 10, 30 to their initial spread position after being squeezed closed by the user.

When the handles 10, 30 are squeezed together, the plunger 80 moves within the dosage chamber 81. The movement of the plunger 80 closes the check valve within the plunger 80 to force ink in the dosage chamber 81 through the check valve within the discharge orifice 82 and out through the discharge orifice 82. When the handles 10, 30 are released by the user, the check valve within the discharge orifice 82 closes to preclude fluid or air being drawn into the dosage chamber 81 through the discharge orifice 82. Simultaneously, the check valve within the plunger 80 opens so that ink is drawn into the dosage chamber 81 through the nipple 76, the hollow head 72, the conduit within the shaft 71, and the conduit with the plunger 80. By turning the dosage adjust valve 86, the length of the shaft 71 is changed. Changing the length of the shaft 71 changes the length of the plunger stroke, and the amount of ink delivered through the discharge orifice 82 is accordingly changed.

In a first preferred method of operation, an appropriately sized needle 64 is selected and received within the vaccine syringe needle fastener 62. The automatic syringe vaccine hose 6 and the syringe ink hose 7 are connected to their respective vaccine and ink sources. Next, the vaccine dose adjust valve 66 and the ink dose adjust valve 86 are rotated to achieve proper dosing. As each of the respective adjust valves 66, 86 is rotated, the functional connection between the adjust valves 66, 86 and their respective syringe shafts 51, 71 moves the initial position of the respective syringe plungers 60, 80 to determine dosage amounts. When adjusted according to dosing requirements, the first syringe handle 10 is rotated about the pivot pin 20 toward the second syringe handle 30 to clear air from the respective hoses 6, 7 and prime the respective syringes 50, 70.

Actuation of the first syringe handle 10 in such a fashion actuates both the vaccine syringe 50 and the ink syringe 70 by forcing both the vaccine syringe shaft 51 and the ink syringe shaft 71 forward. As a result, the vaccine syringe plunger 60 and the ink syringe plunger 80 move toward the needle 64 and the ink discharge orifice 82, respectively, thereby forcing substantially simultaneous expulsion of the respective contents of the vaccine dosage chamber 61 and the ink dosage chamber 81. As the first syringe handle 10 is compressed, the vaccine syringe biasing spring 68 and the ink syringe biasing spring 88 are similarly compressed. Following completion of full compression of the first syringe handle 10 and subsequent release of same, the compressed biasing springs 68 and 88 return the first syringe handle 10 to its original position.

The method of movement of vaccine and ink into their respective dosage chambers 61, 81 is accomplished by any number of devices well known to those skilled in the art of syringes. For instance, an exemplary embodiment of the marking syringe 5 incorporates hollow vaccine and ink shafts 51, 71 and unidirectional diaphragms or check valves within the respective plungers 60, 80 and the respective needle fastener 62 and discharge orifice 82. After actuation of the first syringe handle 10 and injection of vaccine and ink, the return of the first syringe handle 10 to its original position by the respective biasing springs 68, 88 creates a vacuum within the respective dosage chambers 61, 81. The respective unidirectional diaphragms open and close as previously described under this circumstance to draw either vaccine or ink into its respective dosage chamber 61, 81. As the first syringe handle 10 reaches its initial position, the respective dosage chambers 61, 81 are filled with their intended contents and the diaphragm closes, thereby allowing pressurized expulsion of the chamber contents upon actuation of the first syringe handle 10 as previously described.

Figure 2:
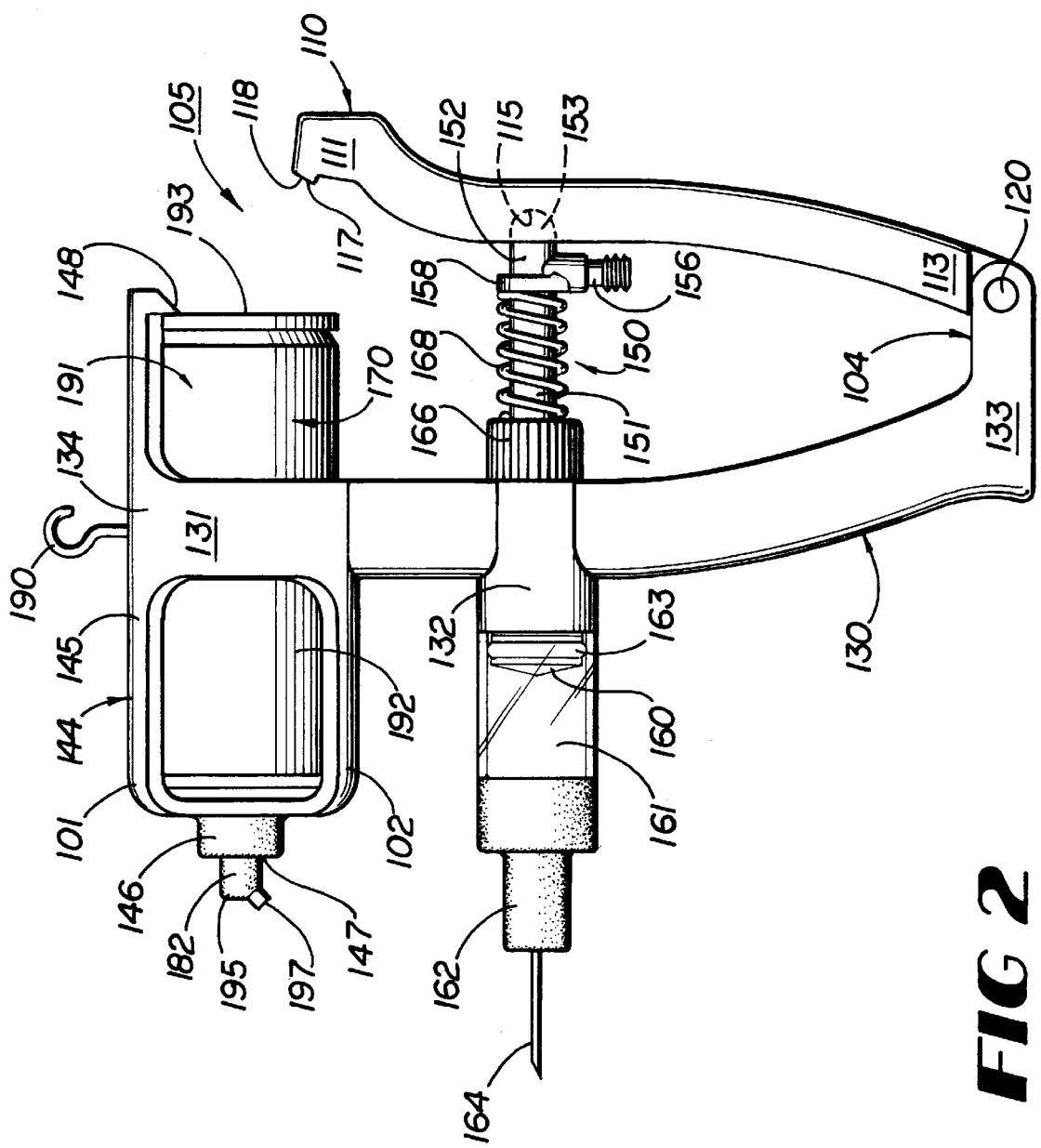
FIG. 2 is an illustration of an alternate embodiment of the present invention in a typical operating environment

FIG. 2 is an illustration of a second preferred embodiment of the present invention. As can be seen in FIG. 2, the marking syringe 105 of the second preferred embodiment of the present invention comprises, generally, a syringe handle 104 operatively connected to a vaccine syringe 150 and an ink dispenser 170. The syringe handle 104 comprises a first syringe handle 110 pivotally connected to a second syringe handle 130. The first syringe handle 110 is elongated, having a first end 111 and a second end 113. The handle 110 is generally shaped for comfortable receipt into the palm portion of the hand of the user. A socket 115 is located intermediate the first end 111 and the second end 113. An ink dispenser interface 117 is located generally adjacent to the socket 115 on handle 110. The handle 110 has a pivot hole at its second end 113.

The second syringe handle 130 of the marking syringe 105 is also elongated and has a first end 131 and a second end 133. The first end 131 of the second syringe handle 130 may securely receive a hook 190 for storage of the marking syringe 105 between uses. The second syringe handle 130 is configured to function as a finger grip for the user. The second end 133 of the second syringe handle 130 is sized to slidably straddle the second end 113 of the first handle 110 and has a pivot hole through its thickness. The second handle 130 includes an integral vaccine syringe collar 132 and an integral ink dispenser collar 134.

During assembly, the second end 133 of the second syringe handle 130 is positioned over the second end 113 of the first syringe handle 110 such that the pivot holes in the ends 113, 133 are axially aligned. Thereafter, a pivot pin 120 is inserted through the aligned holes and appropriately secured therein in any number of ways, including deforming distal ends of the pivot pin 120 so that the diameter of the pivot pin 120 is larger at the points of deformation than the diameter of the pivot pin receiving holes, thereby preventing withdrawal of the pivot pin 120 through the pivot pin receiving holes. After the pivot pin 120 is properly positioned and secured, the second syringe handle 130 rotates about the axis of the pivot pin 120 in a plane defined by the second syringe handle 130 and the first syringe handle 110. In use, the first and second handles 110, 130 are initially in a spread position. The user can then grip the first and second handles 110, 130 and squeeze them into a closed position as the handles 110, 130 pivot about the pin 120.

The vaccine syringe 150 is mounted between the handles 110, 130 by means of the collar 132 on the second syringe handle 130 and the socket 115 on the first syringe handle 110. The vaccine syringe 150 comprises a vaccine syringe head 152 with a ball 153, an extendible vaccine syringe shaft 151, a vaccine syringe biasing spring 168, a vaccine syringe plunger 160, a vaccine dosage chamber 161, a vaccine syringe needle fastener 162, and a needle 164. In order to connect the syringe 150 to the handle 104, the dosage chamber 161 is threaded into the handle collar 132 of handle 130, and the vaccine syringe head 152 is connected to the handle 110 by engaging the ball 153 of the head 152 into the socket 115 of the handle 110 in a well known manner.

The head 152 is hollow and further comprises a vaccine syringe nipple 156 and a vaccine syringe stop flange 158. The vaccine syringe nipple 156 may be integral to the hollow vaccine syringe head 152 and is sized to securely receive a syringe vaccine hose (not shown). Vaccine is delivered to the hollow interior cavity of the head 152 via the vaccine hose which is connected to a vaccine source (not shown). The vaccine syringe stop flange 158 extends laterally about the periphery of the vaccine syringe head 152.

The extendible vaccine syringe shaft 151 interconnects the syringe head 152 and the plunger 160. The shaft 151 has an interior axial conduit (not shown) which communicates at one end with the interior cavity of the head 152 and at the other end with an interior axial conduit (not shown) through the plunger 160. The syringe shaft 151 extends through a vaccine syringe collar 132 of the second syringe handle 130 and into the vaccine dosage chamber 161. In order to vary the amount of dosage, the shaft 151 has a vaccine dosage adjust valve 166. The dosage adjust valve 166 comprises a collar that engages the plunger 160 on one end and is threaded onto shaft 151.

The vaccine syringe plunger 160 slides within vaccine dosage chamber 161. An O-ring 163 creates a liquid tight seal between the periphery of the plunger 160 and the interior wall of the dosage chamber 161. The plunger 160 has a check valve (not shown) within its interior axial conduit that allows liquid to pass only in the direction toward the needle end of the syringe 150.

The vaccine dosage chamber 161 is formed of a translucent or transparent material and is secured at its first end to the vaccine syringe collar 132. The vaccine dosage chamber 161 may be scored with incremental graduations to assist a user in dosage measurements. At its second end, the vaccine dosage chamber 161 removably receives a vaccine syringe needle fastener 162. The vaccine syringe needle fastener 162 is fitted to capture a needle 164. A check valve (not shown) is fitted within the needle fastener 162 to allow liquid flow only out of the needle 164.

A vaccine syringe biasing spring 168 is disposed around the vaccine syringe shaft 151 between the vaccine syringe stop flange 158 and the vaccine dosage adjust valve 166. The biasing spring 168 is a compression spring which serves to return the syringe handles 110, 130 to their initial spread position after being squeezed closed by the user.

When the handles 110, 130 are squeezed together, the plunger 160 moves within the dosage chamber 161. The movement of the plunger 160 closes the check valve within the plunger 160 to force vaccine in the dosage chamber 161 through the check valve within the needle fastener 162 and out through the needle 164. When the handles 110, 130 are released by the user, the check valve within the needle fastener 162 closes to preclude fluid or air being drawn into the dosage chamber 161 through the needle 164. Simultaneously, the check valve within the plunger 160 opens so that vaccine is drawn into the dosage chamber 161 through the nipple 156, the hollow head 152, the conduit within the shaft 151, and the conduit with the plunger 160. By turning the dosage adjust valve 166, the length of the shaft 151 is changed. Changing the length of the shaft 151 changes the length of the plunger stroke, and the amount of medicine delivered through the needle 164 is accordingly changed.

In the second preferred embodiment of the marking syringe, the ink dispenser 170 comprises a self-contained storage unit such as a pressurized canister 191. The self-contained storage unit may take any number of forms well known to those skilled in the art of marking substance apparatus, including, but not limited to, a canister, a jar, a tube, and the like. Further, the self-contained storage unit may be disposable or refillable. The form of the self-contained storage unit is dependent upon the type of ink being utilized. For instance, a pressurized canister may be used to store ink which is suspended in, or in the form of, a compressed gas. Alternatively, a structure such as that used to store caulk may be used to store liquid ink.

To support and retain the self-contained storage unit, the second handle 130 may further comprise an integral retention cage 144 extending from the ink dispenser collar 134. The retention cage 144 may take any number of forms well known to those skilled in the art of mechanical design. It will be appreciated that the form of the retention cage 144 chosen is dependent on the type of self-contained storage unit being utilized.

The ink dispenser interface 117 may also take any number of forms well known to those skilled in the art of mechanical design. For instance, the ink dispenser interface 117 may comprise a direct linkage, such as, for example, the slot 16 described with regard to the first preferred embodiment shown in FIG. 1. Other direct linkages are similarly well known. Alternatively, the ink dispenser interface 117 may comprise a ratcheting mechanism (not shown) for use with a tube of caulk.

Further description of the second preferred embodiment of the present invention will be illustrated by the self-contained storage unit, the retention cage 144, and the ink dispenser interface 117 shown in FIGS. 2–4. In the illustrated embodiment, the self-contained storage unit may comprise a pressurized canister 191, the ink dispenser interface 117 comprises a contact point 118, and the retention cage 144 comprises a body 145, a valve actuator 146, a tip opening 147, and a can detent 148. The pressurized canister 191 may contain ink in the form of an aerosol, in the form of a non-aerosol compressed gas, or the like. The pressurized canister 191 may be mounted to the second handle 130 by means of the collar 134 and the retention cage 144. The pressurized canister 191 comprises a canister body 192 having a bottom surface 193, a valve trigger (not shown), and an ink discharge orifice 182. In order to install the pressurized canister 191 into the handle 104, the canister body 192 is inserted into the handle collar 134 of the second syringe handle 130 and maneuvered into the retention cage 144 until the can detent 148 makes contact with the bottom surface 193 of the canister 191, thereby securely capturing the pressurized canister 191 within the retention cage 144. After secure capture of the pressurized canister 191 within the retention cage 144, the ink discharge orifice 182 extends through the tip opening 147, and the valve trigger is positioned in contact with, or adjacent to, the valve actuator 146. When fully inserted, the retention cage 144 assures that the bottom of the pressurized canister 191 is aligned with the radial path of rotation of the ink dispenser contact point 118 on the second syringe handle 130, as defined by rotation of the second handle 130 about the pin 120.

Figure 4:
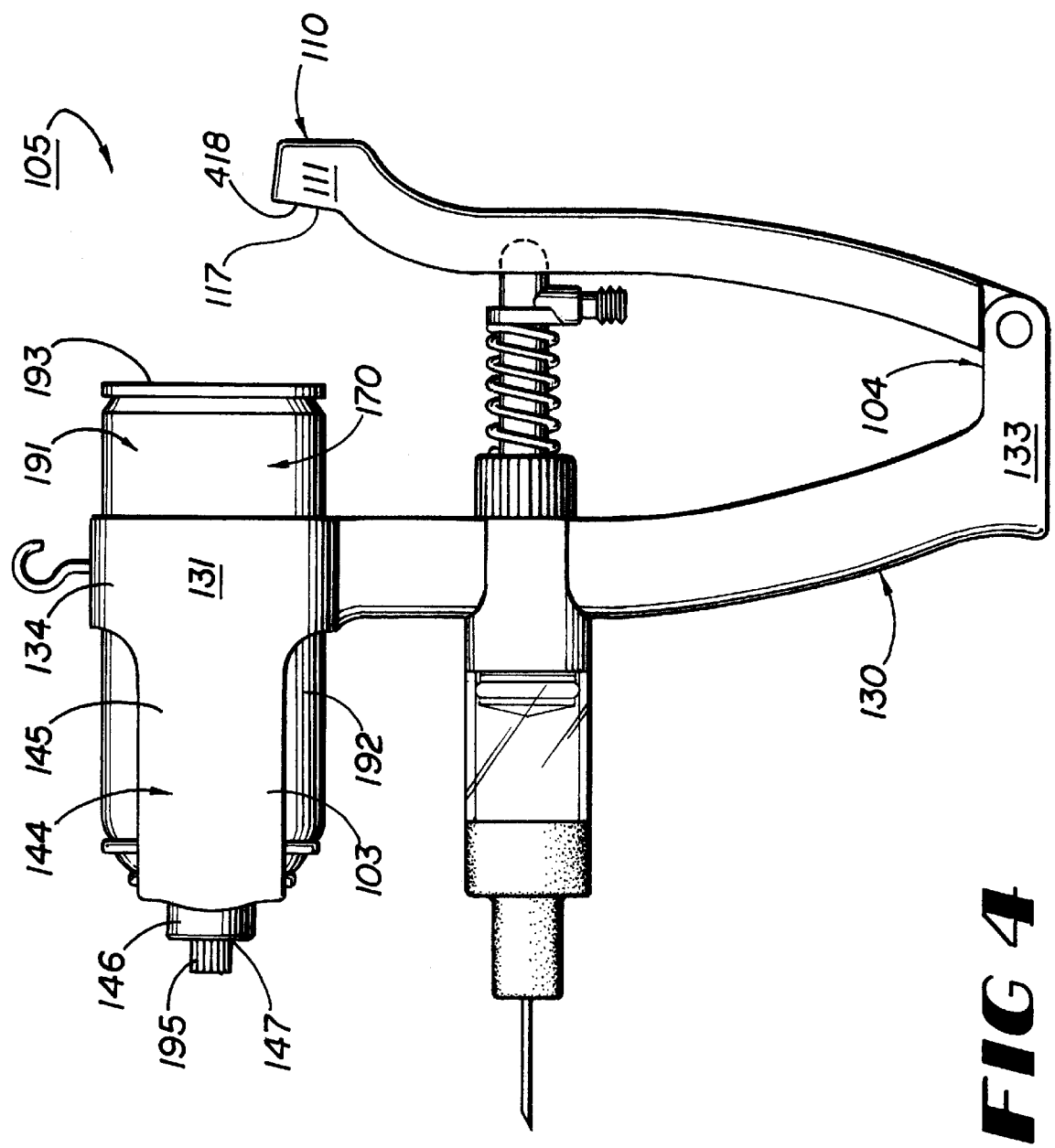
FIG. 4 is an illustration of an alternate embodiment of the present invention in a typical operating environment

The ink dispenser contact point 118 may take any number of forms well known to those skilled in the art. For instance, as shown in FIG. 2, the ink dispenser contact point 118 may be a protrusion extending toward the bottom surface 193 of the pressurized canister 191. Alternatively, as shown in FIG. 4, the ink dispenser contact point 118 may be a substantially flat surface 418.

Also, the retention cage 144 for the pressurized canister 191 may take any number of forms well known to those skilled in the art of can holders. For instance, as shown in FIG. 2, the retention cage 144 may include a top cage member 101 and a bottom cage member 102. Alternatively, as shown in FIG. 4, the retention cage 144 may include a first side cage member 103 and a second side cage member (not shown).

Figure 3:
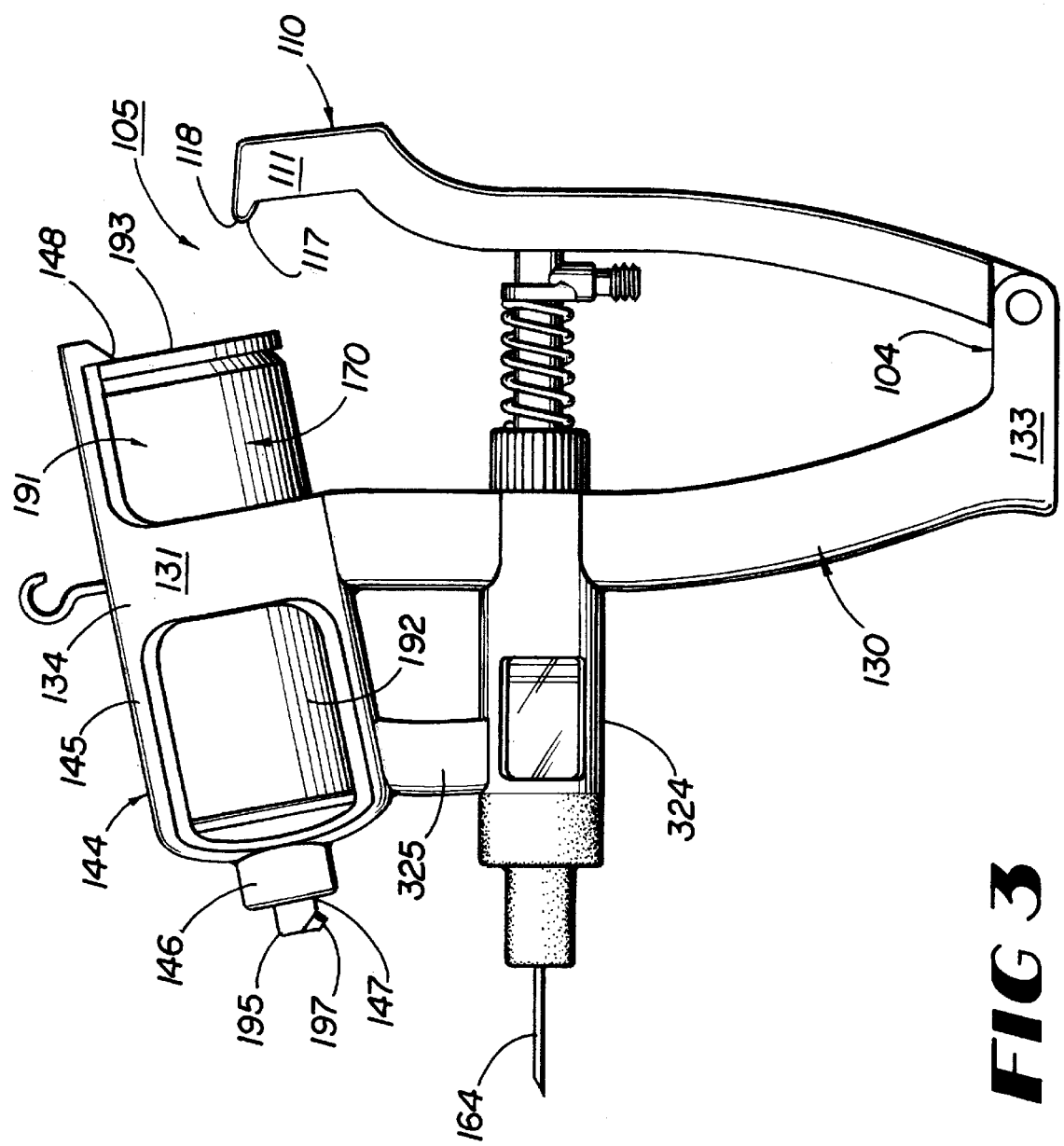
FIG. 3 is an illustration of an alternate embodiment of the present invention in a typical operating environment

Also, the retention cage 144 may be mounted in any number of orientations well known to those skilled in the art of can holders. For instance, as shown in FIG. 2, the retention cage 144 may be mounted generally parallel to the lengthwise linear axis of the vaccine syringe 150. On the other hand, as shown in FIG. 3, the retention cage 144 may be mounted at an angle relative to the lengthwise linear axis of the vaccine syringe 150 in such a position that the retention cage 144 is inclined generally toward the needle 164 of the vaccine syringe 150.

Also, additional structural support may be provided to the retention cage 144, the vaccine syringe 150, or both in any number of forms well known to those skilled in the art of mechanical design. For instance, as shown in FIG. 3, the marking syringe 105 may comprise a syringe cage 324 extending from the vaccine syringe collar 132. The syringe cage 324 provides additional support for the vaccine syringe 150. The marking syringe may also include a support brace 325 to provide additional strength and support between the retention cage 144 and the syringe cage 324.

The pressurized canister 191 further comprises a valve trigger biasing spring (not shown), a spring stop flange (not shown), a valve (not shown), and a delivery passageway (not shown). The ink discharge orifice 182 may be an ink discharge tip 195, which further comprises a spray opening 197. The tip 195 may be created in any number of forms well known to those skilled in the art of pressurized canister tips. For instance, the tip 195 may be an integral component of the pressurized canister 191. A tip 195 suitable for use with the present invention is a tip manufactured by Emson, Inc., of Stratford, Conn. Alternatively, the tip 195 may be formed integrally with the retention cage 144.

Ink may be stored under pressure within the canister body 192. A canister body 192 suitable for use with the present invention is an aerosol can body manufactured by Sexton of Cambridge, Mass. Propellants suitable for providing the necessary pressure are well known to those skilled in the art of aerosol containers. The canister body 192 is communicatively connected with the delivery passageway. The valve trigger opens the valve, allowing pressurized ink fluid to flow into the delivery passageway and to escape through the spray opening 197 to the atmosphere. Preferably, the valve may be a metered valve such as one provided by Emson, Inc., of Stratford, Conn., which allows the release of a predetermined quantity of pressurized fluid. After the valve is depressed and the predetermined quantity of pressurized fluid is discharged, the valve closes and prevents further discharge until the valve is subsequently released and depressed once again.

The spray opening 197 in the ink discharge tip 195 is set at an angle to the axis of the pressurized canister 191. By rotating the ink discharge tip 195, the spray opening 197 may be aimed and thereby the location of the resulting mark with respect to the needle 164 may be controlled.

The valve trigger biasing spring may be disposed between the spring stop flange and the valve trigger. The biasing spring is a compression spring which serves to return the valve trigger and valve to their initial positions after being squeezed open by the user.

When the handles 110, 130 are squeezed together, the first end 131 of the second syringe handle 130 moves toward the first end 111 of the first syringe handle 110 in the previously described manner until the ink dispenser contact point 118 makes contact with the bottom surface 193 of the pressurized canister 191. As the handles 110, 130 are squeezed still closer together, the pressure applied on the bottom of the pressurized canister 191 by the contact point 118 forces the canister body 192 to slide deeper into the retention cage 144. The movement of the canister body 192 causes the valve trigger to be pressed against the valve actuator 146. The pressure on the valve trigger causes the valve trigger to be depressed. The depression of the valve trigger compresses the valve biasing spring and causes the valve to be opened. Ink is propelled out of the canister body 192, through the delivery passageway and out through the spray opening 197 in the tip 195. When the handles 110, 130 are released by the user, the compressed biasing spring expands, forcing the canister body 192 away from the valve actuator 146 and returning the canister body 192 and the valve trigger to their initial positions. This allows the valve to reset in preparation for delivery of the next ink dose.

Although in the embodiment shown, the valve trigger is presumed to be located at the top of the pressurized canister 191, the valve trigger may alternatively be located in any number of positions on the pressurized canister 191 well known to those skilled in the art of pressurized cans. For instance, the valve trigger may be located on the pressurized canister bottom surface 193, or on one side of the pressurized canister 191. It will be appreciated that the design and location of the valve actuator 146 will be dependent upon the location of the valve trigger. Therefore, the valve actuator 146 may be alternatively positioned adjacent to the pressurized canister bottom surface 193. Also alternatively, the valve actuator 146 may be positioned adjacent to a side portion of the canister body 192.

In a second preferred method of operation, an appropriately sized needle 164 is selected and received within the vaccine syringe needle fastener 162. The automatic syringe vaccine hose is connected to the vaccine source. An appropriately sized pressurized canister 191 containing marking ink is loaded into the retention cage. Next, the vaccine dose adjust valve 166 is rotated to achieve proper dosing. As the valve is rotated, the functional connection between the adjust valve and the vaccine syringe shaft 151 moves the initial position of the vaccine syringe plunger 160 to determine the dosage amount. When adjusted according to dosing requirements, the first syringe handle 110 is rotated about the pivot pin 120 toward the second syringe handle 130 to clear air from the vaccine hose and prime the syringe 150.

As described previously, the method of movement of vaccine into the dosage chamber 161 is accomplished by any number of devices well known to those skilled in the art of syringes.

The syringe handle 104 may be actuated by squeezing first and second syringe handles 110, 130 together. Actuation of the first syringe handle 110 in such a fashion actuates the vaccine syringe 150 by forcing the vaccine syringe shaft 151 forward. The forward movement of the shaft 151 causes the vaccine syringe plunger 160 to move toward the needle 164, forcing the contents of the vaccine dosage chamber 161 to begin discharging through the needle 164. Substantially simultaneously with the actuation of the vaccine syringe 150, the ink dispenser 170 is actuated once the ink dispenser contact point 118 reaches the bottom surface 193 of the pressurized canister 191 and the canister body 192 is forced against the valve actuator 146. At this point, continued movement of the first syringe handle 110 causes the canister body 192 to begin to move. As the canister body 192 moves, the valve trigger is depressed by the valve actuator 146, thus actuating the ink dispenser valve. As a result, the marking ink is expelled at substantially the same time as the contents of the vaccine dosage chamber 161 are discharged.

Although, as described, the actuation of the ink dispenser 170 occurs immediately thereafter the actuation of the vaccine syringe 150, it will be appreciated by those skilled in the art that the apparatus of the present invention may be readily altered in such a way that actuation of the ink dispenser 170 occurs immediately prior to the actuation of the vaccine syringe 150 or simultaneously with the actuation of the vaccine syringe 150 without exceeding the scope of the present invention, and that in each of these variations the actuation of the ink dispenser 170 occurs substantially simultaneously with the actuation of the vaccine syringe 150.

As the first syringe handle 110 is compressed, the vaccine syringe biasing spring 168 and the pressurized canister valve trigger biasing spring are similarly compressed. Following completion of full compression of the first syringe handle 110 and subsequent release of same, the compressed syringe biasing spring 168 returns the first syringe handle 110 to its original position, and the compressed canister valve trigger biasing spring returns the canister body 192 to its original position.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto and not limited to the specific embodiments articulated hereinabove.

I hereby claim:

1. A marking syringe, comprising:
   a vaccine syringe including a needle for insertion into an animal;
   an ink dispenser including a discharge orifice for discharging onto the animal; and a syringe handle for capturing the vaccine syringe and the ink dispenser and for allowing substantially simultaneous actuation of both the vaccine syringe and the ink dispenser.

2. The marking syringe of claim 1, wherein the discharge orifice is directionally adjustable.

3. The marking syringe of claim 1, wherein the handle comprises:
   a first handle for capturing the vaccine syringe and the ink dispenser; and
   a second handle for actuating the vaccine syringe and ink dispenser substantially simultaneously.

4. The marking syringe of claim 3, wherein the second handle further comprises an ink dispenser interface for actuating the ink dispenser substantially simultaneously with the actuation of the vaccine syringe.

5. The marking syringe of claim 3, wherein the first handle and the second handle are pivotally connected to each other.

6. The marking syringe of claim 3, wherein the vaccine syringe comprises a vaccine dosage chamber for receiving a vaccine plunger, a vaccine plunger shaft for interconnecting the vaccine plunger and a vaccine syringe head, and a source of vaccine connected to the vaccine syringe head, wherein vaccine is drawn into the vaccine dosage chamber from the vaccine source through the vaccine syringe head, the vaccine plunger shaft, and the vaccine plunger; and the vaccine syringe head is connected to the second handle.

7. The marking syringe of claim 1, wherein the discharge orifice comprises an ink discharge tip having a spray opening.

8. The marking syringe of claim 1, wherein the ink dispenser comprises a canister of pressurized ink.

9. The marking syringe of claim 8, wherein the canister of pressurized ink is an aerosol can.

10. The marking syringe of claim 1, wherein the substantially simultaneous actuation of both the vaccine syringe and the ink dispenser are accomplished by actuation of a trigger, the trigger being functionally interconnected to a source of compressed gas, actuation of the trigger causing a discharge of a quantity of compressed gas from the source of compressed gas so as to actuate both the vaccine syringe and the ink dispenser.

11. A marking syringe, comprising:
   a vaccine syringe including a needle;
   a canister of pressurized ink including a discharge orifice; and
   a syringe handle, wherein the syringe handle comprises a first handle for capturing the vaccine syringe and the ink dispenser and a second handle, pivotally connected to the first handle, for allowing substantially simultaneous actuation of both the vaccine syringe and the ink dispenser.

12. The marking syringe of claim 11, wherein the discharge orifice is directionally adjustable.

13. The marking syringe of claim 11, wherein the vaccine syringe comprises a vaccine dosage chamber for receiving a vaccine plunger, a vaccine plunger shaft for interconnecting the vaccine plunger and a vaccine syringe head, and a source of vaccine connected to the vaccine syringe head, wherein vaccine is drawn into the vaccine dosage chamber from the vaccine source through the vaccine syringe head, the vaccine plunger shaft, and the vaccine plunger; and the vaccine syringe head is connected to the second handle.

14. The marking syringe of claim 11, wherein the discharge orifice comprises an ink discharge tip having a spray opening.

15. The marking syringe of claim 11, wherein the canister of pressurized ink is an aerosol can.

16. A marking syringe, comprising:
  a vaccine syringe, the vaccine syringe comprising a needle, a vaccine dosage chamber for receiving a vaccine plunger, a vaccine plunger shaft for interconnecting the vaccine plunger and a vaccine syringe head, and a source of vaccine connected to the vaccine syringe head, wherein vaccine is drawn into the vaccine dosage chamber from the vaccine source through the vaccine syringe head, the vaccine plunger shaft, and the vaccine plunger;
  an ink dispenser, the ink dispenser comprising an aerosol can having a directionally adjustable discharge orifice, wherein the discharge orifice includes an ink discharge tip having a spray opening; and
  a syringe handle, the syringe handle comprising a first handle for capturing the vaccine syringe and the ink dispenser, and a second handle, pivotally connected to the first handle, for actuating the vaccine syringe, wherein the first handle includes an ink dispenser interface for allowing substantially simultaneous actuation of the ink dispenser with the actuation of the vaccine syringe, and wherein the second handle is connected to the vaccine syringe head.

* * * * *